US012661033B2

(12) United States Patent
Yelin et al.

(10) Patent No.: US 12,661,033 B2
(45) Date of Patent: Jun. 23, 2026

(54) SYSTEM FOR IN VIVO MEASUREMENTS OF TYMPANIC MEMBRANE VIBRATION

(71) Applicant: TECHNION RESEARCH & DEVELOPMENT FOUNDATION LIMITED, Haifa (IL)

(72) Inventors: Dvir Yelin, Haifa (IL); Matan Hamra, Kfar Yona (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 235 days.

(21) Appl. No.: 18/032,339

(22) PCT Filed: Oct. 18, 2021

(86) PCT No.: PCT/IL2021/051229

§ 371 (c)(1),
(2) Date: Apr. 18, 2023

(87) PCT Pub. No.: WO2022/079721

PCT Pub. Date: Apr. 21, 2022

(65) Prior Publication Data

US 2023/0380725 A1 Nov. 30, 2023

Related U.S. Application Data

(60) Provisional application No. 63/093,244, filed on Oct. 18, 2020.

(51) Int. Cl.
| | |
|---|---|
| *A61B 5/12* | (2006.01) |
| *A61B 1/227* | (2006.01) |
| *A61B 5/00* | (2006.01) |

(52) U.S. Cl.
CPC ............. *A61B 5/126* (2013.01); *A61B 1/227* (2013.01); *A61B 5/0066* (2013.01); *A61B 5/6817* (2013.01)

(58) Field of Classification Search
CPC ............................. A61B 5/126; A61B 5/0066
See application file for complete search history.

(56) References Cited

U.S. PATENT DOCUMENTS

| | | |
|---|---|---|
| 2013/0100455 A1 | 4/2013 | Tearney et al. |
| 2014/0176960 A1* | 6/2014 | Kemp ................ G01B 9/02091 |
| | | 356/479 |
| 2019/0368929 A1* | 12/2019 | Zhang .................... G01J 3/0275 |

FOREIGN PATENT DOCUMENTS

WO 2008131082 A1 10/2008

OTHER PUBLICATIONS

Grechin, et al. Imaging acoustic vibrations in an ear model using spectrally encoded interferometry. Optics Communications, 2018, 407: 175-180. (Year: 2018).*

(Continued)

*Primary Examiner* — Michelle M Iacoletti
*Assistant Examiner* — Alexandria Mendoza
(74) *Attorney, Agent, or Firm* — Daniel J. Feigelson

(57) ABSTRACT

A system for noninvasive in vivo functional imaging of the human ear and measurement of nanometer scale motion of the tympanic membrane under various acoustic excitations, and identification of vibration patterns that vary between human subjects in response to sound. By combining spectrally encoded imaging with phase-sensitive spectral-domain interferometry, high-resolution imaging of the membrane surface is obtained within a fraction of a second, through a handheld imaging probe. The detailed physiological data obtained allows measuring a wide range of clinically relevant parameters for patient diagnosis, and provides a new tool for studying middle and inner ear physiology. Use of a line measurement technique, without mechanically scanning the probe beam, enables characteristics of the membrane vibration to be measured, in a time scale of tenths (Continued)

of a second, thereby reducing the possibility of inaccuracy because of movements of the hand-held instrument.

21 Claims, 12 Drawing Sheets

(56) References Cited

OTHER PUBLICATIONS

Kim, et al. Picometer scale vibrometry in the human middle ear using a surgical microscope based optical coherence tomography and vibrometry system. Biomedical optics express, 2019, 10.9: 4395-4410. (Year: 2019).*

Matan Hamra, Ariel Weigler, Shadi Shinnawi, Mauricio Cohen Vaizer, and Dvir Yelin "Imaging tympanic membrane vibrations (Conference Presentation)", Proc. SPIE 10854, Endoscopic Microscopy XIV, 108540W (Mar. 4, 2019); https://doi.org/10.1117/12.2508487 (Year: 2019).*

Pawlowski ME, Shrestha S, Park J, Applegate BE, Oghalai JS, Tkaczyk TS. Miniature, minimally invasive, tunable endoscope for investigation of the middle ear. Biomed Opt Express. May 27, 2015;6(6):2246-57. doi: 10.1364/BOE.6.002246. PMID: 26114043; PMCID: PMC4473758. (Year: 2015).*

Buunen, et al., "Laser-Doppler velocity meter applied to tympanic membrane vibrations in cat.", The Journal of the Acoustical Society of America, 1981, 69.3: 744-750. (Mar. 1, 1981).

Hamra et al., "Rapid imaging of tympanic membrane vibrations in humans", Biomedical Optics Express, vol. 11, No. 11, pp. 6470-6479, Nov. 2020.

* cited by examiner

SYSTEM FOR IN VIVO MEASUREMENTS OF TYMPANIC MEMBRANE VIBRATION

FIELD

The present application relates to the field of measurement of the acoustic vibrations of the tympanic membrane, especially using spectrally encoded interferometry.

BACKGROUND

Diagnosing hearing problems requires assessment of the multiple factors involved in the mechanical transduction of sound into the inner ear. These tests are some of the most common diagnosis procedures in the world, where approximately 450 million people (over 5% of the world population) suffer from some sort of a disabling hearing loss. In most cases, early detection and intervention could significantly reduce the negative impact of hearing problems; in some types of conductive hearing loss (CHL) such as otosclerosis and otitis media, for example, preventive treatment may include prescription of various drugs that could save the need for hearing aids or surgical intervention.

A range of technologies are available today for hearing diagnosis, including pure tone audiometry and pneumatic otoscopy; however, most techniques are relatively subjective and provide only partial information that limits effective diagnosis. More objective approaches for functional hearing diagnosis include measuring the auditory brainstem response (ABR), otoacoustic emissions (OAE's) under different acoustic stimuli, and acoustic reflections of single and multiple harmonic stimuli.

Several experiments have demonstrated the feasibility of optical interferometry to measure acoustic vibrations; Laser Doppler vibrometry (LDV) was proven effective for measuring nanometer-scale motion at a single point of the tympanic membrane. By scanning the membrane point by point, optical coherence tomography (OCT) allowed 3D imaging of an ex vivo tympanic membrane, including its acoustic vibrations map, and several measurement methods of the dynamics and structure of the tympanic membrane in vitro, have been reported. Recently, phase-sensitive OCT allowed in-vivo measurement of the middle ear and the tympanic membrane vibrations in human subjects at multiple locations.

Despite these developments, in-vivo imaging of both amplitude and phase across the continuous membrane surface could be challenging using beam scanning techniques, mainly due to the inevitable motion artifacts that occur during the slow data acquisition. Scan-free methods such as stroboscopic holography have been demonstrated ex vivo on surgically exposed membranes within a fresh temporal bone; however, in vivo imaging with this technique may be challenging due to the relative complexity of the holographic imaging apparatus.

In vivo high-speed nanometric imaging of a vibrating surface is described in U.S. Pat. No. 8,838,213 to G. J. Tearney et al, for "Apparatus and Method for Obtaining and Providing Imaging Information Associated with at least One Portion of a Sample, and Effecting such Portions" one of the present inventors being a co-inventor on that patent.

Adding low-coherence, phase-sensitive spectral-domain interferometry allowed interferometric spectrally encoded endoscopy (ISEE) to image nanometric-scale surface vibrations. Briefly, ISEE measures the spectral interference between a reference and spectrally encoded reflections from the target tissue. Under acoustic stimulations, the axial tissue motion induces wavelength-dependent phase shifts that are then captured by a high-speed spectrometer. By slowly scanning the imaging line across the tissue, the full vibration pattern is recovered with high lateral resolution and nanometric axial sensitivity. Such a technique has been used to image a model of the human tympanic membrane in the article by O. Ilgayev and D. Yelin, entitled "Phase-sensitive imaging of tissue acoustic vibrations using spectrally encoded interferometry," published in Opt. Express 21, 19681 (2013), and in the article by S. Grechin and D. Yelin, entitled "Imaging acoustic vibrations in an ear model using spectrally encoded interferometry," published in Optics Communications 407, 175-180 (2018).

The disclosures of each of the publications mentioned in this section and in other sections of the specification, are hereby incorporated by reference, each in its entirety.

SUMMARY

The present disclosure describes new exemplary systems for an interferometric spectrally encoded endoscopy (ISEE) system capable of in vivo imaging of the tympanic membrane in human subjects which would enable diagnostic results to be obtained rapidly in real time. The need for a method which is rapid and has a very fast measurement time arises because of the very tiny movements of the tympanic membrane which need to be measured. Consequently, the measurement system must be maintained in a very stable position during the duration of the measurement of the membrane motion. The quicker the measurement, the less likely it is that an unintended motion of the measurement instrument relative to the subject's membrane, occurring during the measurement scan, will disturb the measurement rendering it unreliable or incorrect. The accuracy of any diagnosis on the subject is highly dependent on the reliability and accuracy of the instrument used. Thus, preventing any unintended motion requires a compact instrument that can be easily handled by the clinician, and prior art systems lack these properties. The present disclosure attempts to provide novel systems and methods that overcome at least some of the disadvantages of prior art systems and methods In vivo imaging of tympanic membrane dynamics in response to various acoustic stimuli would be invaluable for studying the function of this important organ. Being physically connected to the malleus, the first of the three ossicles, the tympanic membrane dynamics is strongly affected by the entire chain of mechanical sound conduction and consequently by the mechanical properties of the inner ear as well.

The optical setup of the imaging probes of the present disclosure, allow single-hand operation by the clinician, and is an advance on previous bench-top setups for performing ISEE, both in the type of measurements enabled by the system, and in overcoming the optical problem of directing the beam through the long and narrow auditory canal, and in consideration of the fact that the entire measurement needs to be performed through several limiting apertures along the auditory canal, through the speculum of the otoscope, and the limited overall size of the handheld instrument.

Light from a broadband source, such as a fiber-coupled broadband superluminescent diode (SLD) array is split by a 50/50 fiber coupler to the sample and reference arms of a Michelson interferometer. At the sample arm, light is collimated by a focal-length lens, optionally scanned by a single-axis galvanometric scanner, diffracted by a transmission diffraction grating, magnified by an achromatic telescope and focused on the tissue surface using an additional imaging lens. Light reflected from the tissue is propagated back through the same optical path, coupled into the single-mode fiber, which serves as an effective pinhole for confocal imaging, and measured by a high-speed line camera within a custom-built spectrometer. Additional components within the probe include an optical shutter, a conventional otoscope with an optical window replacing its original lens, and a robust handgrip for guiding the speculum into the ear canal. Widefield illumination of the sample is thus obtained using the integral white-light illumination of the otoscope.

As an alternative to a broadband diode source, emitting a range of wavelengths, a swept wavelength light source may be used, in which the wavelength is swept as a function of time, to generate a wavelength chirp for inputting to the system. In such a case, the diffracting element temporally disperses a spot of light along the tissue surface, the spot having a varying wavelength according to the time varying wavelength of the swept source.

The system can capture the full vibration patterns of the human tympanic membrane in response to an arbitrary acoustic stimulus, thanks to the combination of spectrally encoded endoscopy with phase-sensitive spectral-domain low-coherence interferometry. The higher spectral resolution of the spectrometer (0.025 nm) compared to that of the imaging probe (0.075 nm) allows the system to record spectral interference from every sample location, and while the optical bandwidth that encodes this location allows relatively low axial resolution (approximately 940 μm), the relative phases of the modulated spectra could be captured with extremely high accuracy, yielding axial sensitivities of only a few nanometers. Such nanometric sensitivity, when combined with a high-speed heterodyne line measurements of up to 70 kHz, allows the direct detection of the axial acoustic oscillations of a three-dimensional surface, within a fraction of a second. This is an important feature in the presently described system which enables its effective use in such a high sensitivity, hand-held measurement instrument.

In comparison to OCT, which is capable of high-resolution imaging of the membrane structure and thickness, as well as deeper structures of the middle ear, the advantages of the present ISEE-based system stem mainly from the single-shot line acquisition, that results in considerably faster imaging, less motion artifacts and simpler imaging probes. For example, in the article describing an OCT system, by W. Kim et al, entitled "Picometer scale vibrometry in the human middle ear using a surgical microscope based optical coherence tomography and vibrometry system," published in Biomed. Opt. Express 10, 4395 (2019), there is described that capturing a single-frequency vibration pattern of the human tympanic membrane in vivo required 95 seconds for completing a single scan. In contrast, the ISEE instrument of the current disclosure, enables such a scan of the whole tympanic membrane to be achieved within only 0.2 second, faster by more than two orders of magnitudes than the OTC system. Furthermore, ISEE imaging at 11 different sound frequencies using the presently described ISEE system, requires only 2.3 seconds, and single-line measurements require even shorter times. Such rates are particularly important in the clinic, where fast, comprehensive functional measurements are often essential for timely diagnosis. The need to scan only a single axis also allows smaller imaging probes that could be held and operated by a single clinician. Additional advantages of the present ISEE instrument is the continuous lateral scanning, allowing continuous full 2D sampling of the membrane surface without the interpolation typically used in OCT. For 3D imaging, however, ISEE is limited by its axial resolution, which is typically lower by 1-2 orders of magnitude compared to OCT due to the small bandwidth that encodes each lateral location. Hence, when compared to OCT, ISEE cannot directly measure the tympanic membrane thickness, may be affected by reflections from ossicles beneath the membrane, and is therefore less suitable for high-resolution 3D imaging of the outer and middle ear. The axial nanometric sensitivity is similar to that of OCT, as phase-sensitive spectral-domain interferometry is common to both modalities.

A number of purely technical issues have been addressed in the presently disclosed instruments, in order that the system could achieve widespread and effective use in the clinic. Firstly, a real-time visual feedback can be provided to the clinician, improving the physical contact between the otoscope speculum and the patient's ear canal, and by using faster acquisition rates and polarization-maintaining optics.

Secondly, in order to obtain meaningful physiological data of clinical significance, the system is calibrated according to protocols that are commonly used for hearing tests. For example, while the frequency-sweep data records the true axial displacements of the tympanic membrane, its magnitude does not reflect the true frequency response of the membrane because the true excitation sound amplitudes are generally unknown, and depend mainly on the frequency response curve of the earphones used. An effective calibration procedure with high-quality broadband earphones and sound systems fully integrated into the modified otoscope system can provide such clinically definitive measurements. While such calibration is required for measuring the exact membrane mechanical properties, non-calibrated, but repeatable, measurements are still useful for clinical diagnosis, for example by comparing the frequency response curves between different patients under identical excitation waves.

Thirdly, measuring mechanical nonlinearities in the ear, such as those caused by the stapedius reflex, would also be valuable from a clinical perspective. Such previously described measurements were challenging mainly because of the noisy environment of the laboratory. Using a calibrated system with adequate acoustic isolation of the patient ears, may allow detection of the stapedius reflex, and the imaging of this phenomenon with high spatial resolution.

Finally, the high acquisition speed and relative simplicity of the present ISEE-based instrument may also allow straightforward assessment of an array of clinical conditions such as observation of changes in the tympanic membrane following surgery or trauma. In the clinic, the proposed system could also help diagnosing otosclerosis and otitis media, and may even help identifying and studying otoacoustic emissions in patients with tinnitus.

The optical system is thus suitable for high-resolution in vivo imaging of tympanic membrane vibrations. With nanometric axial sensitivity and single-shot line acquisition, the full vibration maps of the tympanic membrane may be recorded noninvasively within a fraction of a second, revealing vibration patterns that vary between different healthy human subjects. These new capabilities can serve as a powerful tool for patient diagnosis, providing a set of highly sensitive measurements that could detect numerous physiological and clinically relevant parameters.

According to a novel implementation of the instruments of the present disclosure, the optical system does not need to include any mechanical scanning capability, but uses only the spectrally dispersed line generated by the diffraction grating, in order to generate a single line which can be directed such that it passes through the umbo.

When a mechanical scanner is incorporated into the instrument, for use in providing 2-dimensional plots of the tympanic membrane, it can also be used for positioning the line on its exact target through the umbo. Even though this alignment can generally be performed by simple movement by the operator of the entire instrument, using visual observation through the imaging facility of the instrument, such a mechanical scanner could be used in an automatic feedback system, to ensure that the beam line is kept in its correct position, despite operator movements, or movements of the subject's internal ear parts because of pulse or other internal movements. Such a system uses image processing routines performed on the image of the tympanic tissue, to identify the umbo position, and a signal from the image processing system to provide feedback to the scanner motor to maintain the intended position of the line on the umbo.

The need for measurement along a single line, of at least one additional point besides the umbo, arises from the need to ascertain that any lack of motion or limited motion of the umbo itself under any excitation conditions, does not arise from a global problem with the tympanic membrane, that may for instance have a low flexibility which is the cause of the poor motion response at the umbo. Abnormal umbo-membrane motion may also indicate excessive stiffness of the umbo, which may be caused by abnormal sound conduction through the entire middle-ear ossicles.

The advantage of single line measurement is that it now becomes possible, by using chirped frequency exciting acoustic inputs, or by a short acoustic pulse, to determine the dependence of the amplitude of motion of any predefined line on the tympanic membrane, as a function of frequency during the course of single sweeps, therefore decreasing by an order of magnitude or more, the measurement time, compared with the time for measurements of complete two dimensionally scanned images. This is important not only because of the overall increased efficiency of performing such otometric testing, but also because any motion during the measurement, whether of the patient him/herself, or any involuntary bodily motion such as due to the patient's pulse, may render the measurement defective, such that the quicker the measurement, the more useful the instrument to the medical practitioner.

The optical performance of the system thus allows single-hand operation, and effective imaging of various vibration patterns is possible under different harmonic stimuli. The system can thus extract relevant functional parameters by employing a single-line measurement technique, which permits rapid measurements of the membrane response to continuously varying sound amplitudes and frequencies.

There is thus provided, in accordance with an exemplary implementation of the instruments described in this disclosure, a system for determining the vibrational characteristics of a line across a tympanic membrane of a subject, the system comprising:

(a) a light source adapted to input into the system, a beam of the light having a range of wavelengths;

(b) a diffracting element configured to spectrally disperse the beam of light along the line;

(c) a lens system configured to focus the line of spectrally dispersed light through the auditory canal of a subject, such that it impinges on the tympanic membrane of the subject; and (d) a control system adapted to determine from a spectrometric analysis of light resulting from the interference of the spectrally dispersed light reflected from the tympanic membrane with a reference beam, the vibrational amplitude of motion of the tympanic membrane as a function of position along the line.

Such a system may further comprise (i) a source of illumination in the visible region, disposed such that the tympanic membrane is illuminated, and (ii) a lens system positioned to provide widefield imaging of the illuminated tympanic membrane. In such a case, the system may further comprise a widefield camera adapted to enable operator guidance of the position of the line of the beam of light across the tympanic membrane.

Any of the above described systems may further comprise a sound source adapted to apply an acoustic signal to the tympanic membrane. Such a sound source may be configured to output the acoustic signal amplitude modulated over a range of from 0 to 90 dB.

Additionally, the acoustic signal may contain frequencies in a range of from 0 to 20 kHz. That range of frequencies may be obtained by frequency modulation of the acoustic signal. Alternatively, the range of frequencies may be obtained by application of a pulse of the acoustic signal, the pulse containing signals over the range of frequencies.

Use of such an applied acoustic signal system enables the frequency response of separate parts of the tympanic membrane to be determined. The acoustic signal may be applied to the opposite ear of the subject to that on which the vibrational characteristics are determined.

In any of the above systems, the line of illumination may include the Umbo region, or it may include the malleus.

According to yet another implementation of the above described systems, the system may further comprise a mechanical scanning element configured to scan the line of light across the membrane in a direction other than that of the line of light, to acquire information of the two-dimensional vibrational characteristic of the tympanic membrane. The scanning element may alternatively be adapted to position the line of light onto the membrane. In the latter instance, the system may further comprise a feedback system inputting the position of the line on the membrane, and outputting a signal to align the scanning element such that the line of light maintains its position in spite of mutual motion between the system and the membrane. In such a system, the position of the line of light on the membrane may be determined using image processing of a camera image of the membrane.

In any of the above described systems, the diffracting element and lens system may be disposed within an otoscope, or within an endoscope.

According to further implementations of these systems, such a system may further comprise a polarization controller inserted into each of the optical paths of the spectrally dispersed light reflected from the tympanic membrane and the reference beam, such that the interference contrast of the light is improved. Alternatively, the light source may have a predefined polarization, and the paths along which the light passes essentially maintain the polarization of the light passing therethrough.

Finally, in any of the above described systems, the light source may comprise a swept wavelength source, such that the diffracting element temporally disperses a spot of light along the line, the spot having a varying wavelength according to the time varying wavelength of the swept source.

BRIEF DESCRIPTION OF THE DRAWINGS

The present invention will be understood and appreciated more fully from the following detailed description, taken in conjunction with the drawings in which.

DETAILED DESCRIPTION

Figure 1:
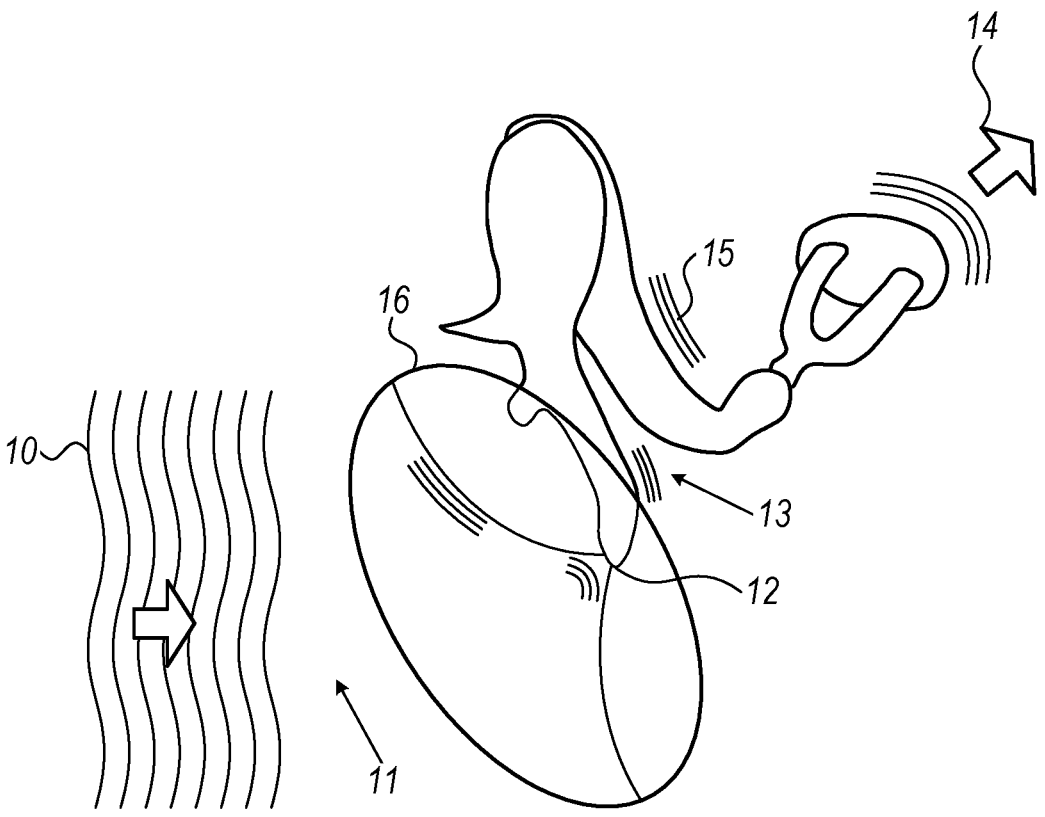
FIG. 1 illustrates schematically drawings of the ear showing the physiologically relevant parts to the currently described systems and methods.

Reference is now made to FIG. 1, which illustrates schematically a drawing of the ear showing the parts physiologically relevant to the currently described systems and methods. The acoustic pressure wave 10 passes through the long and narrow ear canal 11, and impinges on the tympanic membrane 16. The umbo 12 is the point behind which the malleolus auditory ossicle of the middle ear 13, contacts the tympanic membrane, passing the vibrations 15 on to the inner ear 14.

Figure 2:
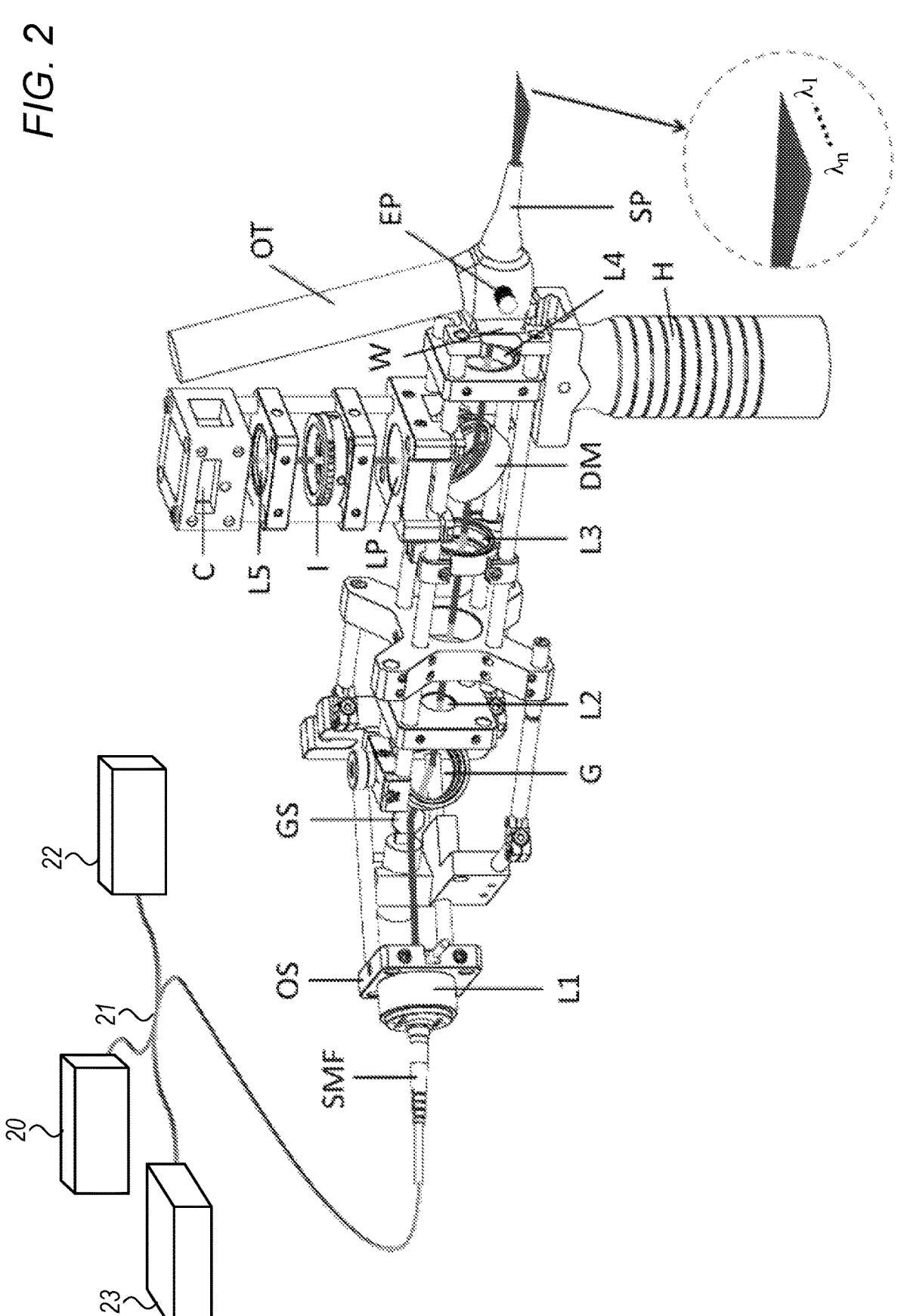
FIG. 2 illustrates schematically an exploded isometric view of an exemplary instrument showing the optical setup of the imaging system allowing single-hand operation by the clinician.

Reference is now made to FIG. 2 which shows an exemplary instrument of the present disclosure, having an imaging system designed to allow single-hand operation by the clinician of the instrument, showing typical components that may be used. However, it is to be understood that the specific component descriptions are only suggested types, and are not intended to be limiting, and that any alternative optical components suitable for the task could be used. Light from a fiber-coupled broadband (50 nm, 840 nm center wavelength) superluminescent diode array 20 is split by a 50/50 fiber coupler 21 to the sample and reference arms 22 of a Michelson interferometer. At the sample arm, light from the single mode fiber SMF is collimated by a 11 mm focal-length lens L1, optionally scanned by a single-axis galvanometric scanner GS, if fitted, diffracted by a 1200 lines/mm transmission grating G, magnified (2×) by an achromatic telescope L2, L3 and focused on the tissue surface using an additional imaging lens L4 having a 100 mm focal length. This optical setup enables transmission of the incident optical signal into the auditory canal. Light reflected from the tissue is propagated back through the same optical path, coupled into the single-mode fiber SMF, which serves as an effective pinhole for confocal imaging, and is measured by a high-speed line camera, such as the model spL4096-70 km, having a 70 kHz maximum line rate supplied by Basler AG of Ahrensburg, Germany. The camera is installed within a custom-built spectrometer 23. Additional components within the probe includes an optical shutter OS, a conventional otoscope OT with an optical window W replacing its original lens, and a robust handgrip H for guiding the speculum SP into the ear canal, where the incident optical illumination is shown spectrally dispersed from wavelengths $\lambda_1$ to $\lambda_n$. Widefield illumination of the sample is obtained using the integral white-light illumination of the otoscope.

Real-time widefield imaging of the tissue is attained using a dichroic mirror DM (transmission threshold 650 nm), a low-pass filter LP, (90% transmission below 750 nm), a Fourier-plane iris I, an additional lens L5, having a 40 mm focal length, and a small imaging camera C, having a 30 Hz frame rate. At the reference arm 22, a delay line (not shown in FIG. 2) is used to adjust the axial imaging depth, placing the virtual reference plane RP behind the tympanic membrane for preventing mirror artifacts. Two polarization controllers (not shown) are used at the sample and reference fibers to improve interference contrast. Alternatively, a polarized light source and polarization-maintaining fibers may be used.

Sound stimulus may be provided using a PC sound card through an earphone EP that is attached to the otoscope pneumatic port. The excitation sound amplitude can be estimated by placing a calibrated microphone within an ear model that simulates the human ear canal.

In one exemplary implementation of such a system, the field of view is a square of 4.5×4.5 mm$^2$. The line-camera imaging speed is adjusted according to the exact acoustic stimulation, and is chosen to maintain twelve measurements per single acoustic period for all frequencies. For example, a full scan with 2000 Hz excitation can be acquired at 24 kHz line rate, resulting in a total of 400 acoustic periods per single frame acquired during 0.2 s. System sensitivity, namely the ratio between the signal from a perfect reflector and the noise floor, at this imaging speed is approximately 69 dB, and the axial imaging range is limited mainly by twice the Rayleigh range (approximately 6.6 mm), which is somewhat smaller than the 9 mm coherence range determined by the spectrometer resolution (0.034 nm). The axial sensitivity, i.e. the accuracy of determining the axial location of the membrane, is approximately 5 nm, determined by the effective width of the measured membrane. The lateral optical resolution is approximately 12.5 μm (FWHM of the line-spread function), but can be digitally reduced in the horizontal dimension to approximately 30 m due to the 32-pixel window of the Hilbert transformation. As a result, a single 4096×5150-pixel raw image acquired by a single y-scan of the galvanometric scanner, if activated, can yield a three-dimensional surface having 128×128 lateral resolvable points sampled by 256×256 pixels. Membrane axial motion is computed by multiplying the phase difference between the Hilbert transforms of subsequent spectral interferograms by $4\pi/\lambda_i$ where $\lambda_i$ denotes the encoding wavelength at each location along the spectrally encoded line. Motion artifacts due to axial probe motion can be removed by filtering out the resulting uniform, non-periodic spectral phase shifts.

Figure 3:
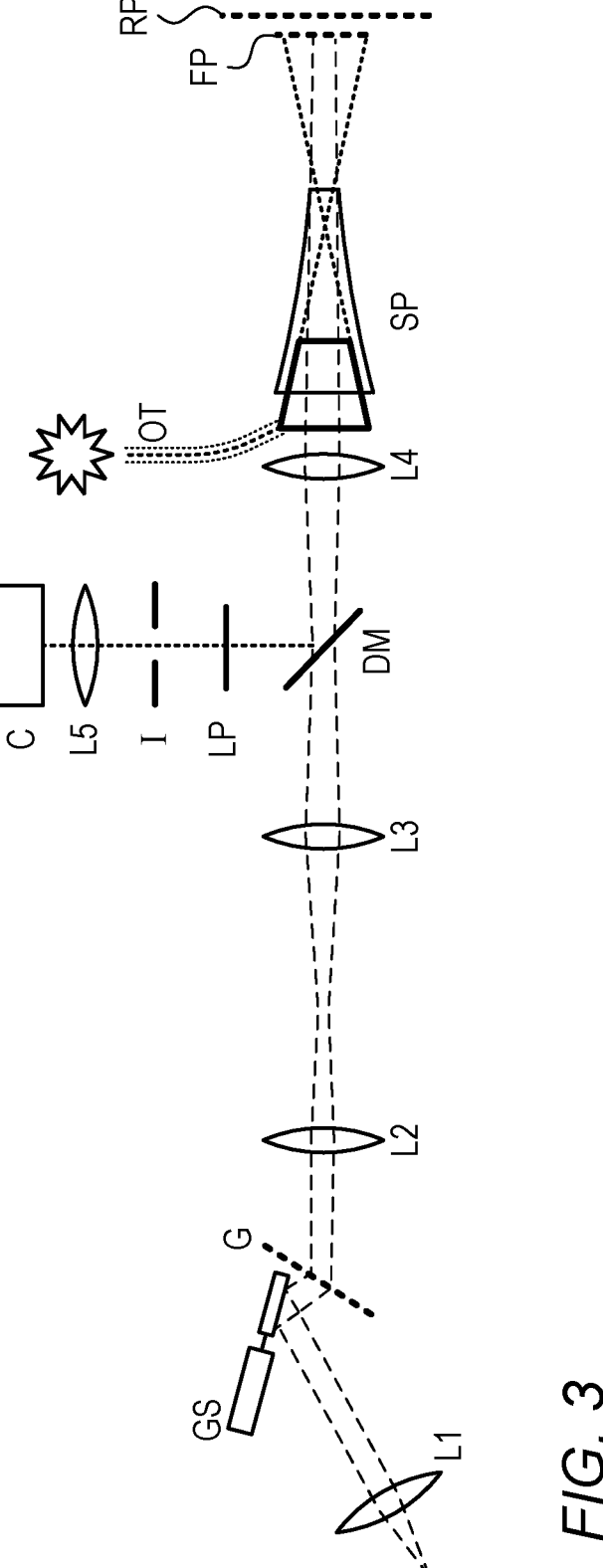
FIG. 3 shows a simplified drawing of the optical system used in the instrument of FIG. 2, so that the optical arrangement can be more readily followed.

FIG. 3 shows a simplified drawing of the optical system used in the instrument of FIG. 2, so that the optical arrangement can be more readily followed.

Figure 4A:
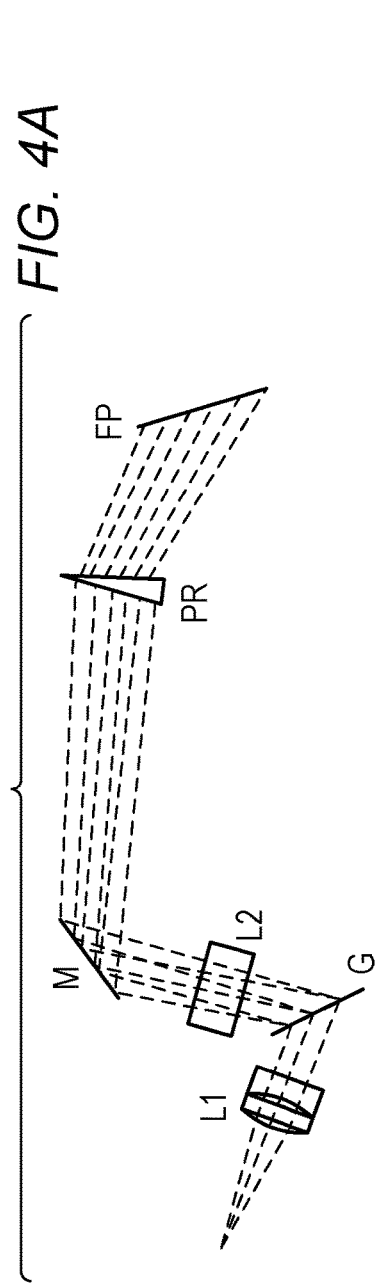
FIGS. 4A and 4B show a compact ISEE instrument for hands-free operation, with FIG. 4A showing ray tracing of a suggested optical design and FIG. 4B showing a schematic illustration of the probe end of the instrument inside the ear canal.
Figure 4B:
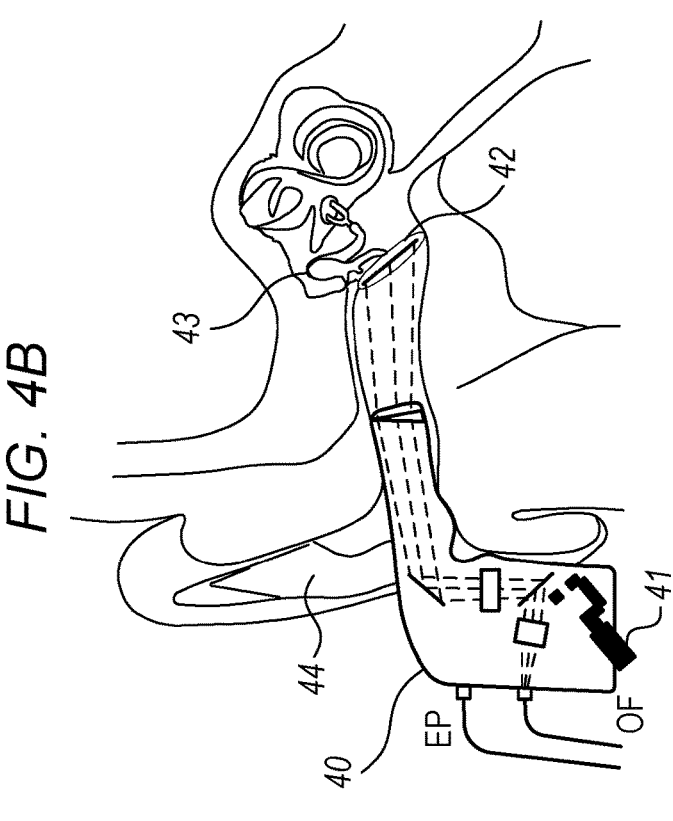

Reference is now made to FIGS. 4A and 4B, which show an alternative compact ISEE based instrument, without an otoscope, for hands-free operation. FIG. 4A shows a suggested optical design using ZEMAX™ ray tracing, with L1, L2—lenses; G—diffraction grating; M—mirror; PR—prism; FP—focal plane. FIG. 4B is a schematic illustration of the probe 40 inside the ear canal, showing the pinna 44, the tympanic membrane 42 and the ossicles 43. A miniature electric motor 41 is shown for rotating the grating for scanning the tympanic membrane, when full frame images are needed rather than a single line scan. EP is the earphone, and OF is the optical fiber.

Figure 5:
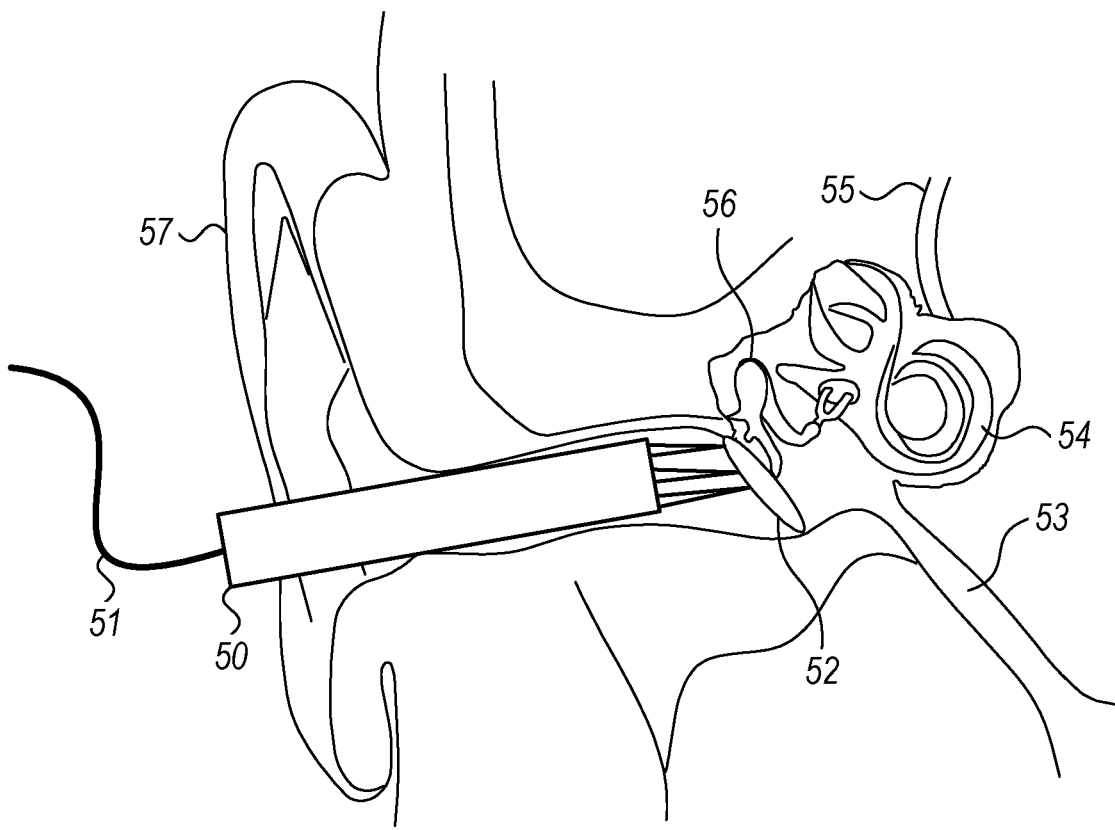
FIG. 5 shows how a compact ISEE instrument for hands-free operation can be constructed in an endoscope configuration that can be inserted into the auditory canal.

Reference is now made to FIG. 5, which shows how a compact ISEE system of the present disclosure, for hands-free operation, can be constructed in a simple endoscope configuration 50 that can be inserted into the auditory canal, with only a single optical fiber 51 trailing therefrom. The anatomic features shown are similar to those of previous drawings, and show the pinna 57, the membrane 52, the ossicles 56, the chochlea 54, the auditory nerve 55 and the Eustachian tube 53.

Figure 6:
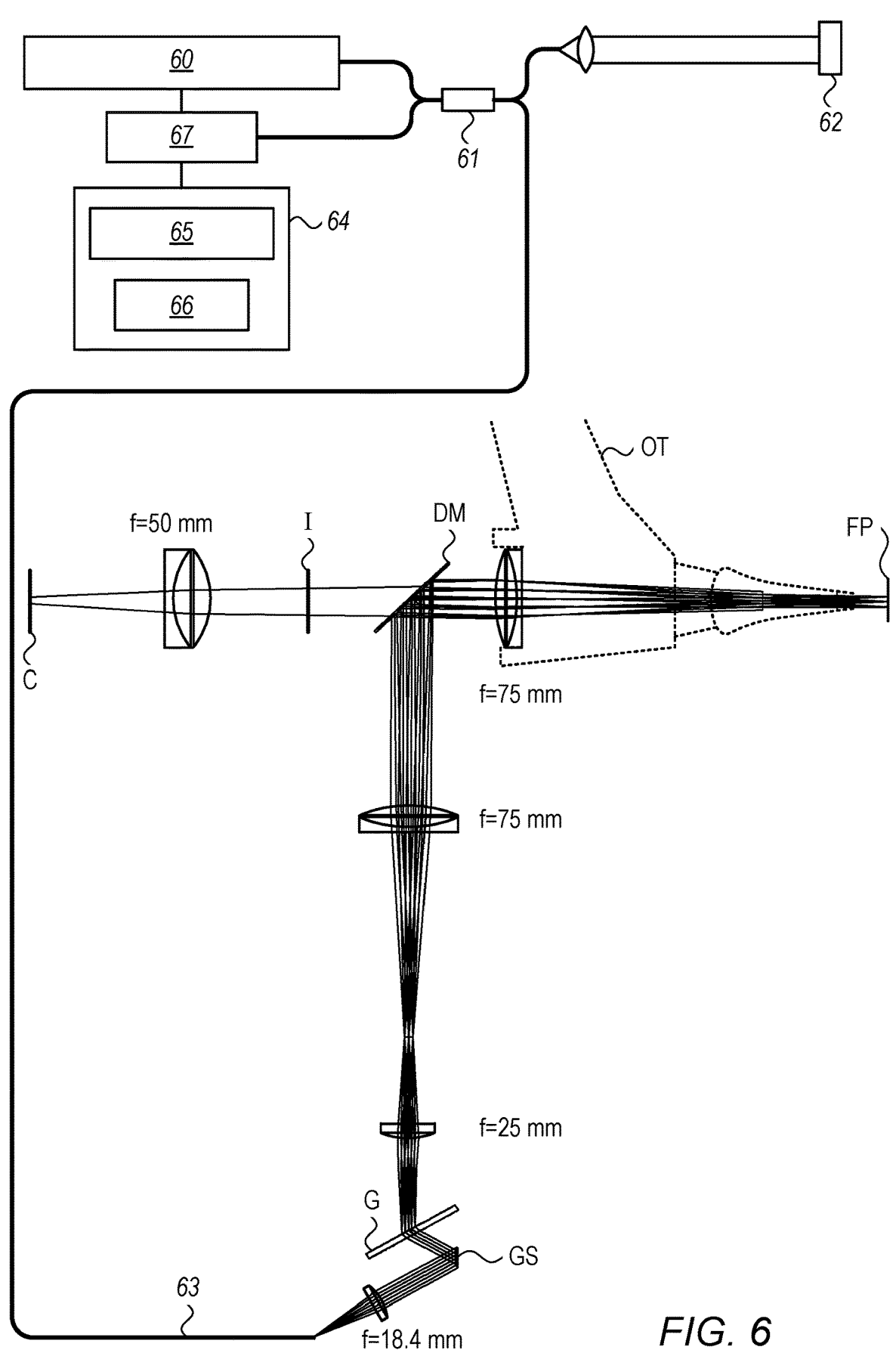
FIG. 6 shows the complete optical path design of another compact instrument design, using a complex three-lens solution to solve the problem of ensuring insertion of the beam into the narrow auditory channel.

Reference is now made to FIG. 6, which shows the optical path design of another compact instrument design, whose external view will be shown in FIG. 7. In the optical design of FIG. 6, a complex three-lens solution is used, because of the difficulties of ensuring insertion of the beam into the narrow auditory channel, while ensuring a scan over the whole of the membrane through the long and narrow auditory canal. The overall system has a Michelson interferometer comprising a broadband source, typically from 810 to 860 nm, a fiber coupler 61, from which the input and output signals are transmitted to the instrument through a single mode fiber, typically having a numerical aperture of 0.13, a reference arm 62, and the spectrometer 67, whose output is read by the computer system 64, which may have a data acquisition unit 65, and can also provide the acoustic stimulation through a sound card 66. The optical system includes, besides the calculated lenses shown in the drawing, a grating G, a galvanomic scanner GS, a dichroic mirror DM, the focal plane of the optical system FP being positioned close to the tympanic membrane plane, an iris I and an imaging camera C. The optical system is integrated with a conventional otoscope OT.

Figures 7A, 7B:
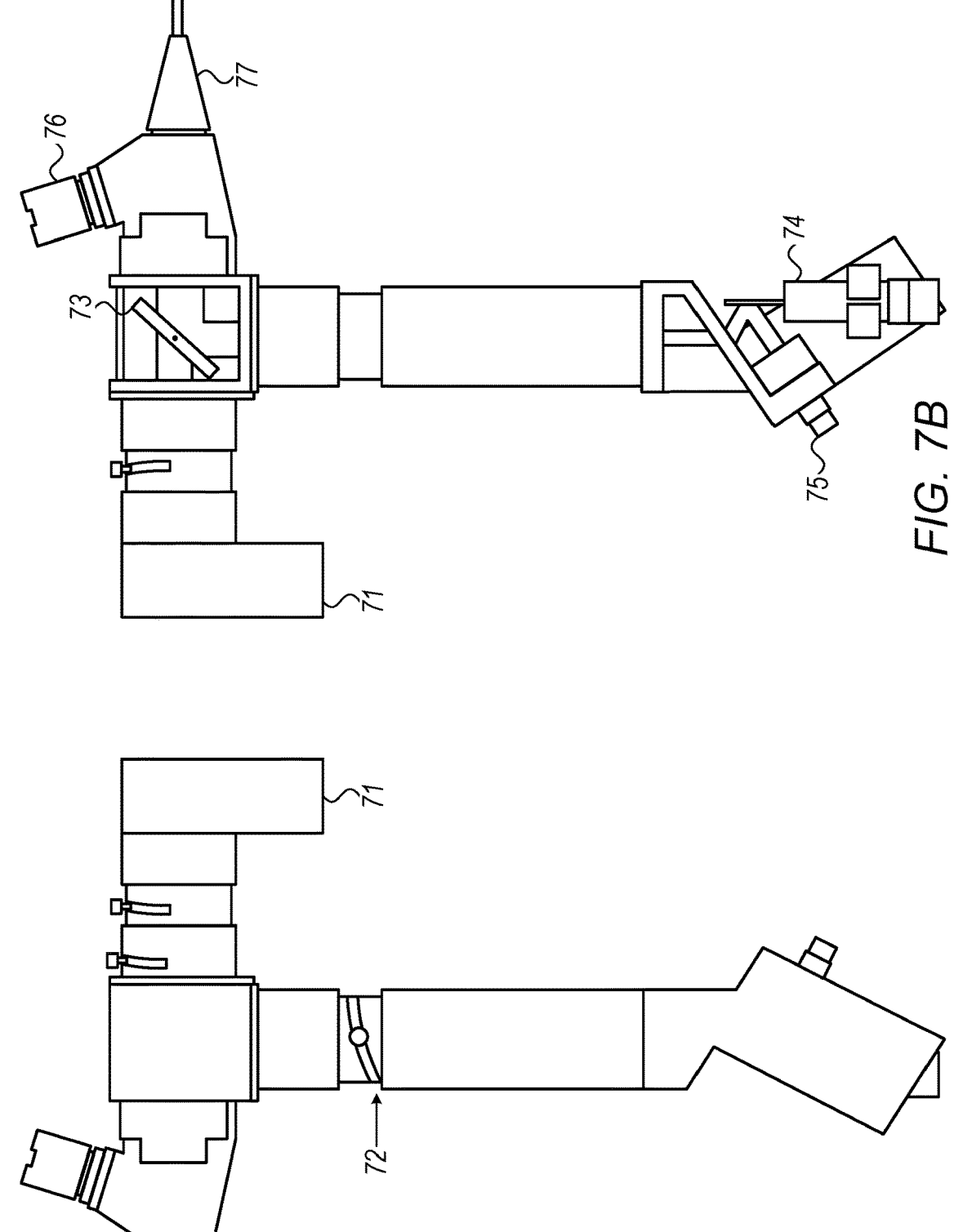
FIGS. 7A and 7B are external views of an exemplary compact hand-held ISEE system, using the optical design shown in FIG. 6.

Reference is now made to FIGS. 7A and 7B, which show the outlines from both sides of a complete highly compact instrument constructed using the optical design of FIG. 6 in an otoscope. The instrument includes the fiber connector 75, the motor 74 for moving the galvanometric scanning mirror, a focusing control 72 for adjusting the length of the optical telescope system, a dichroic mirror 73 for reflecting the beam towards the focusing system for directing the beam onto the subject's ear drum through the speculum 77, and a camera 71 for providing direct images of the ear drum. A miniature otoscope 76 is shown for operation with the system.

There are now shown in FIGS. 8A, 8B, 8C to FIG. 13, the results of a number of in vivo measurements, to show the abilities of the presently described systems. The figures all show screen images and system computer graphs of the measured results, to illustrate the abilities of the presently described instruments shown in the previous drawings. It should be emphasized that in FIGS. 8A, 8B, 8C and FIG. 9, there are illustrated the overall two-dimensional scan measurement abilities of the instruments incorporating a galvanometric mechanical scanning mirror, even though the important clinical advantage of the presently described instruments lies in the ability to perform a single line spectrally dispersed scan through the umbo, without the need for galvanometric scanning, therefore enabling the generation of meaningful results in a minimum of time, thereby reducing the effects of instrument motion or vibration, by reducing the time for obtaining meaningful measurements.

Four sets of measurements performed are shown:
(i) Single two-dimensional imaging of a subject with 2000 Hz pure-tone 90 dB excitation.
(ii) Two-dimensional imaging under different pure-tone 90 dB excitation between 750 Hz and 5500 Hz.
(iii) Single-line measurement with continuous amplitude sweep 0-90 dB. and
(iv) Single-line measurement with a continuous frequency sweep (sound amplitude not calibrated).

Figures 8A, 8B, 8C:
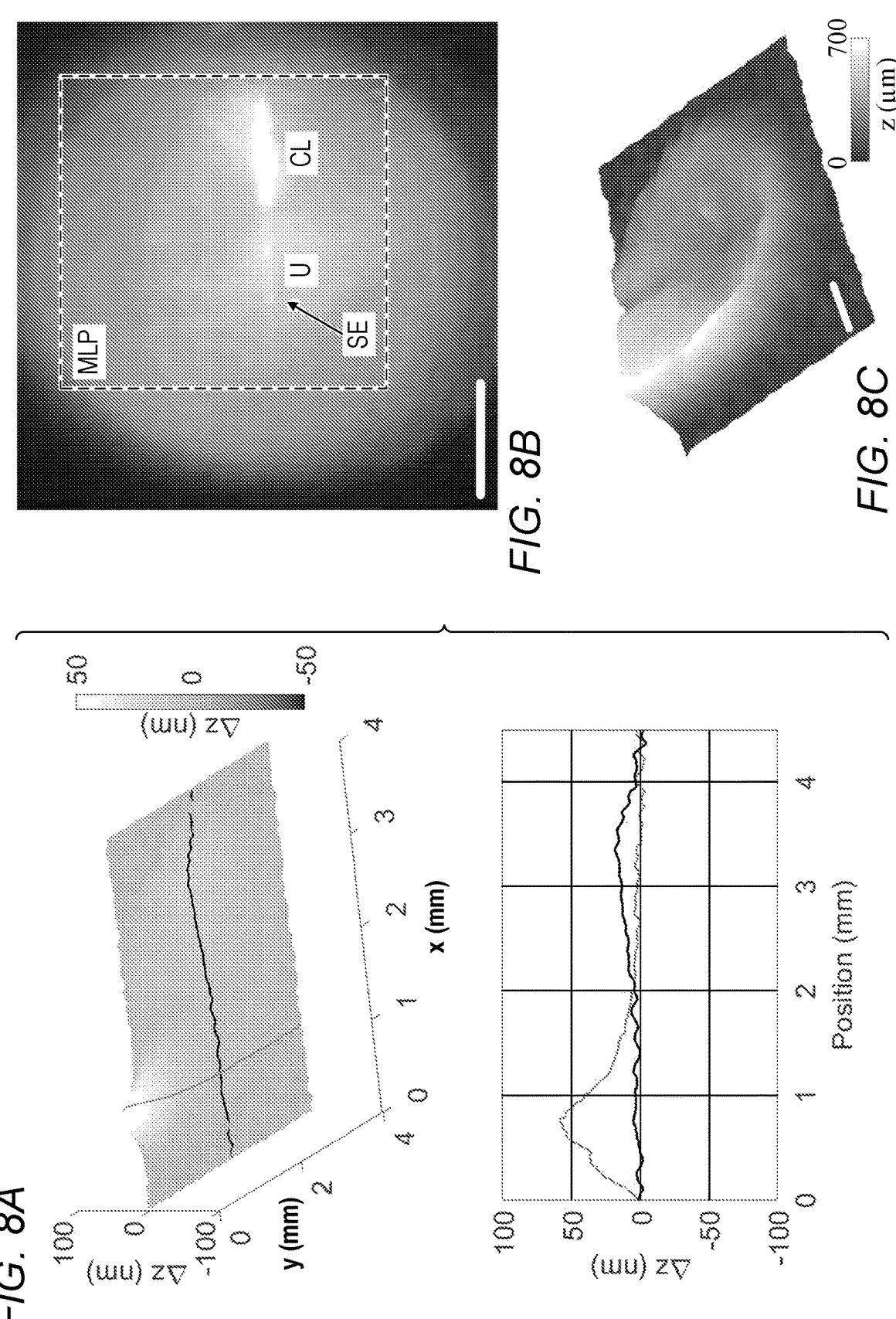
FIGS. 8A, 8B and 8C show various results obtained from two dimensional imaging of the excitation of the tympanic membrane of a subject, using the previously shown systems, including mechanical scanning to obtain the two-dimensional images.

For in vivo imaging, the subject was seated next to the imaging probe which was supported by a jointed arm for reducing its effective weight and allowing continuous imaging with minimal motion artifacts. After guiding the speculum into the (right) ear canal, a full vibration image, as shown in FIG. 8A was captured by a single y-scan of the galvanometric mirror during 200 ms under pure-tone 2000 Hz acoustic excitation. The lateral, more pronounced, line in the image, corresponds to the approximate CL-U direction, while the almost vertical, fainter line corresponds to the U-MLP direction. The same field of view was also imaged by the widefield camera, as shown in FIG. 8B, including the umbo point (U), the cone of light (CL), the malleus lateral process (MLP) and the faint reflections from the spectrally encoded line (SE). The scale bars represent 1 mm. The white dashed-line square corresponds to the approximate field of view in FIG. 8A. The two cross-sections of the vibration movie from the top 3D panel, are shown in the lower panel of FIG. 8A, the CL-U line, which is the fairly flat response, and the U-MLP line having the large amplitude motion at its left end of the image. The characteristic curved surface of the tympanic membrane is clearly visible in the height map shown in FIG. 8C, which was computed using a windowed Fourier transformation at each sample location. The axial resolution in this image was 940 μm, and depended on the imaging bandwidth at each sample location (approximately 0.33 nm).

Several features are worth noting in the movie frame shown in FIG. 8A. First, the curved and angled membrane made imaging of its most posterior part (left-hand side of the frame) challenging, mainly due to the weak reflections from that region. In contrast, the strong reflections from the cone of light often saturated the spectrometer camera and limited the dynamic range. Second, vibration amplitudes at the lateral process of the malleus were as high as ±50 nm, notably higher compared to those at the cone-of-light and the umbo. The malleus itself, a rigid bone that touches the tympanic membrane at the umbo and with its lateral process, appears to be vertically translating and rotating, as evident by the approximately 900 oscillation difference between these two points. And third, at 2000 Hz the membrane did not oscillate uniformly; rather, the regions of the cone of light and the malleus lateral process oscillated ahead of the umbo region by approximately 90°, and the resulting oscillation waves appears to propagate inward, from these regions toward the umbo.

Figure 9:
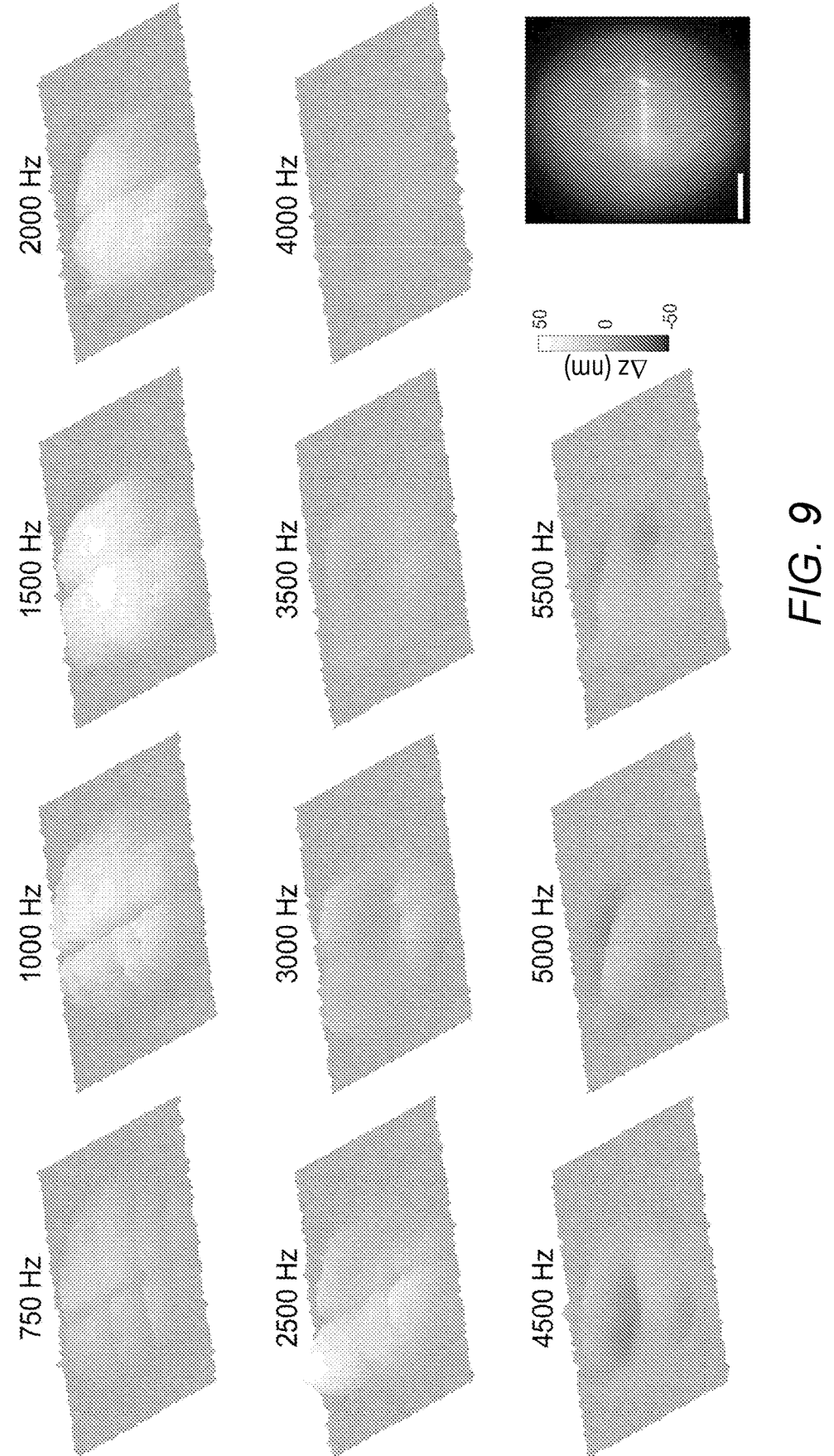
FIG. 9 shows two-dimensional vibration patterns of the tympanic membrane obtained using the instruments of the present disclosure, under different excitation frequencies, of from 750 Hz. to 5,500 Hz.

In agreement with previously known measurements, including the above referenced Kim article, the vibration patterns of the tympanic membrane changes considerably under different excitation frequencies, as shown in FIG. 9. As the sound frequency increases, surface vibrations vary from uniform in-phase motion up to 1500 Hz, through various asymmetric patterns at 2000-3500 Hz, to patterns with some rotational symmetry at 4000-5500 Hz. These in vivo patterns differ from the in vitro patterns measured in excised human temporal bone, most likely due to the obvious physiological and mechanical differences between living and excised tissues. The currently measured vibration patterns appear mostly similar to those measured in humans by endoscopic OCT, except for the rotational patterns revealed in FIGS. 8 and 9 for frequencies above 4000 Hz. The oscillation amplitudes at the umbo region are in the range 0-50 nm, in agreement with measurements performed on human fresh temporal bones (0-50 nm), as described in the article by J. T. Cheng et al, entitled "Wave motion on the surface of the human tympanic membrane: Holographic measurement and modeling analysis," published in The Journal of the Acoustical Society of America 133, 918-937 (2013).

Some of the image artifacts visible in FIGS. 8A, 8B, 8C and 9 include a prominent vertical dark line caused by loss of signal at a narrow spectral band, most likely due to polarization deviation between the sample and the reference, which was not perfectly compensated across the entire encoding bandwidth. Occasional horizontal lines (visible mainly in FIG. 9 at 750 Hz, 1000 Hz and 2500 Hz excitations) were caused mainly by occasional unintended axial motion of the probe relative to the membrane, causing temporal fringe washout that could not be recovered by data processing.

In order to extract meaningful clinical data that would be compatible with conventional methods for hearing diagnosis, the spectrally encoded line may be positioned at the center of the field of view, constantly illuminating both the umbo region and the cone of light. Without any vertical scanning, the system can now continuously measure the membrane response to various excitation parameters, where the raw data includes the rapidly varying spectral interferogram (x-axis) as a function of time.

Figure 10A:
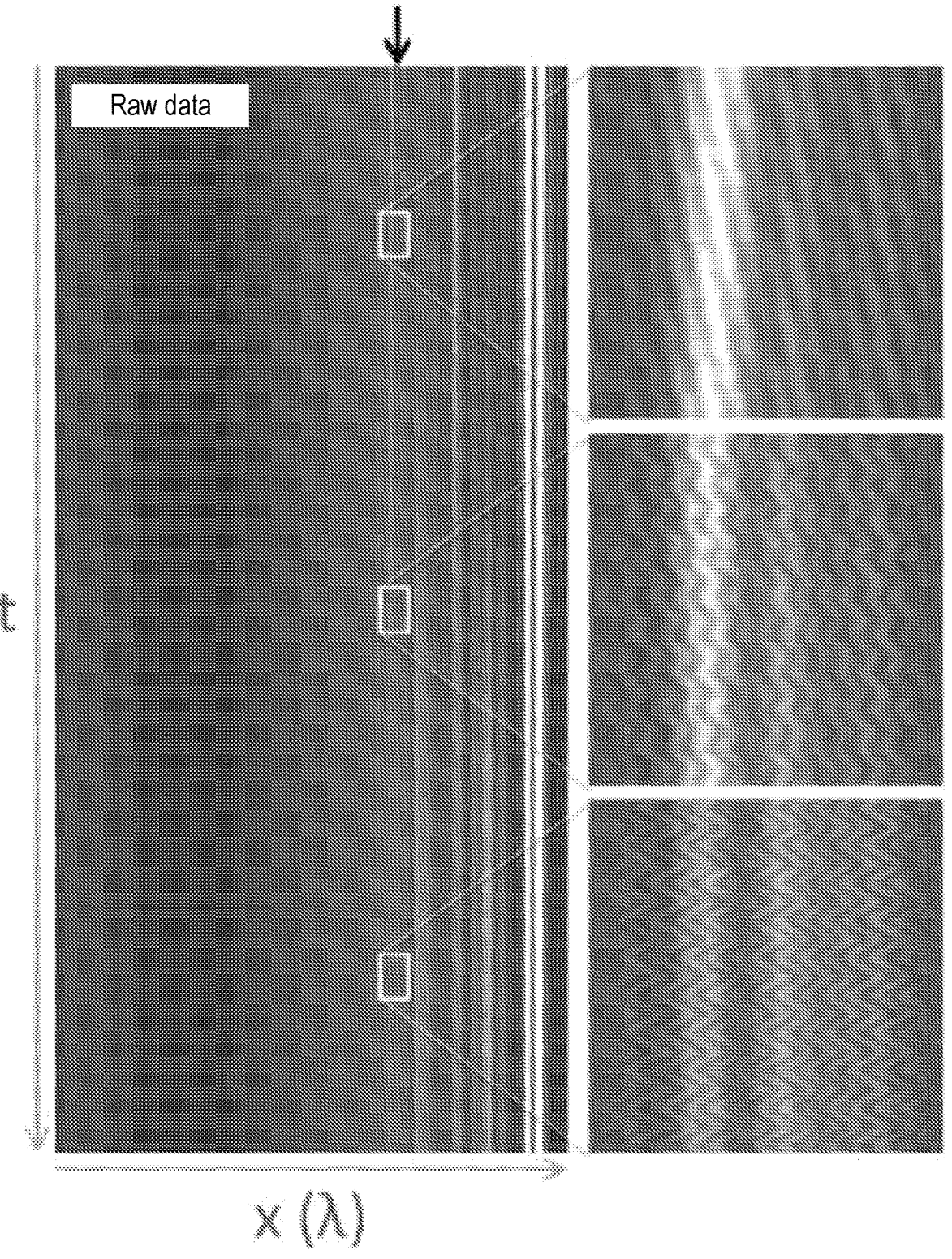
FIGS. 10A and 10B illustrate schematically the ability to assess membrane oscillation linearity in response to increasing sound stimulus, without using mechanical scanning, using a single line scan.
Figure 10B:
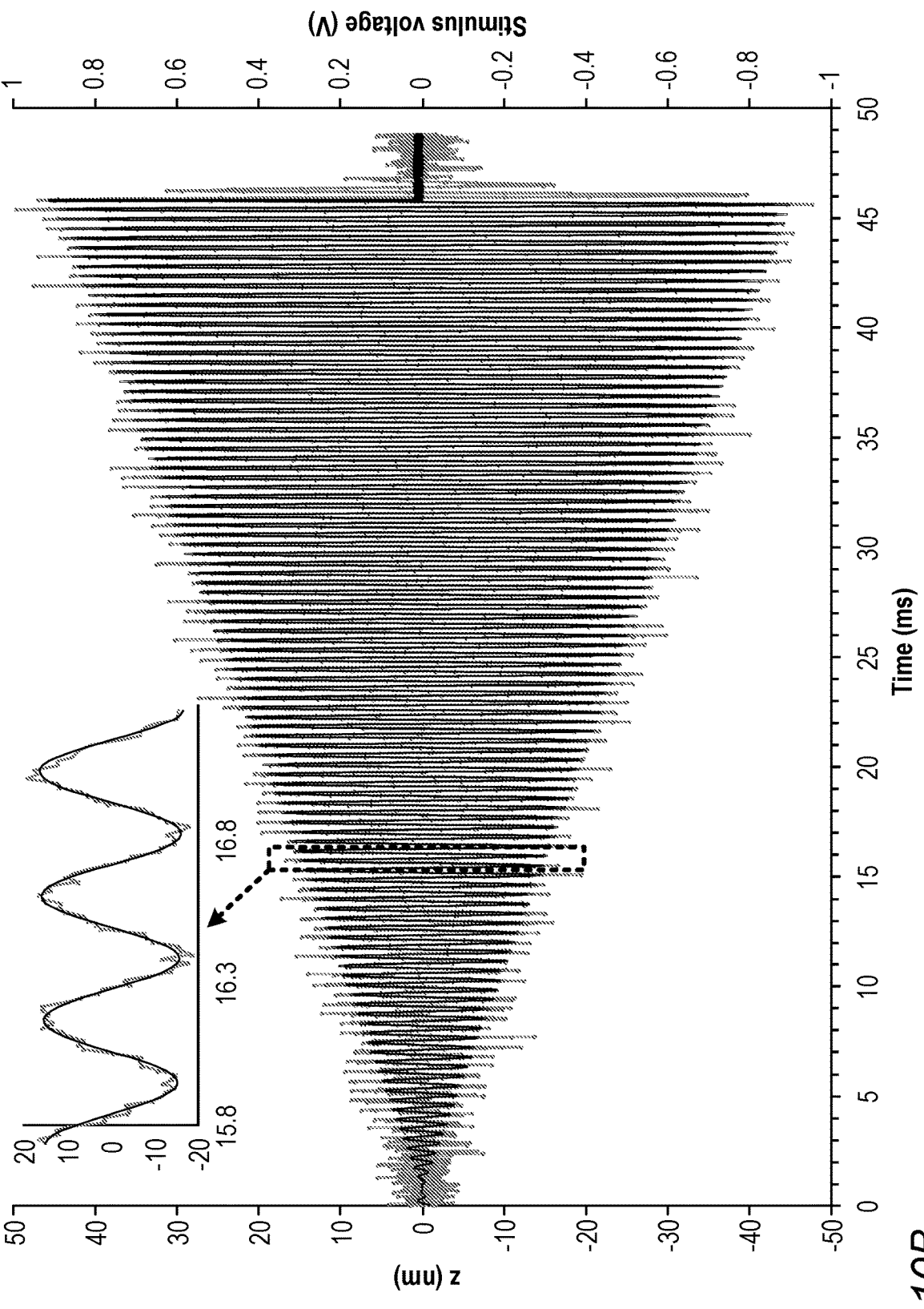

Reference is now made to FIGS. 10A and 10B, which illustrate schematically the ability to assess membrane oscillation linearity in response to increasing sound stimulus, without using mechanical scanning, such that a single line scan is generated. In the results shown, the carrier frequency was set to 2000 Hz and the amplitude was increased linearly from zero to 90 dB over a period of 46 ms. The raw data file (4096×2500 pixels total), as shown in FIG. 10A, shows a spectral interferogram from a single line on the sample (horizontal x axis) as a function of time (vertical axis). The axial harmonic (2000 Hz) movements of the membrane are visible as continuous periodic shifts of the interference fringes (50 kHz acquisition line rate, 25 pixels per single acoustic period). The increased amplitude as function of time is clearly visible in three high-magnification views (white rectangles) of the raw data, showing fringe oscillation at the varying amplitudes.

The vibration amplitude, shown in FIG. 10B, at a single location on the membrane, as marked by an arrow in FIG. 10A, fits well to the acoustic excitation wave, as shown in the essentially overlapping plots in the graph at the top of the full scan plot, demonstrating the linear relation ($R^2=0.983$) between sound amplitude and membrane displacement. Once excitation amplitude reached its maximum amplitude after 46 ms, it abruptly dropped to zero. Though difficult to discern the separate acoustic excitation curve and the membrane displacement curve in the imaged plot of FIG. 10B, the difference can be just discerned at the top and bottom edges of the plots. The excitation curve follows a linearly increasing level, while the membrane displacement, while generally tracking the excitation amplitude, inevitably has slight amplitude variations due to noise and measurement accuracy effect, as is discerned at the top and bottom edges of the plots.

It is noted from the graph of FIG. 10B that the membrane oscillation decayed only after approximately 2 ms. after the 46 ms. point at the end of the input acoustic excitation wave, which can be used as a measure of the response time of the membrane to an impulse. Such an impulse could also be a square wave pulse of acoustic excitation. The rise time or the decay time of the membrane provides a measure of the membrane flexibility, which may be the cause of a poor motion response at the umbo. Abnormal umbo-membrane motion may also indicate excessive stiffness of the umbo, which may be caused by abnormal sound conduction through the entire middle-ear ossicles. Care must be taken to ensure that any artifacts due to ringing of the sound source are either eliminated by use of a high quality sound generation source, or that any part of the decay time due to the sound source is taken into account in the measurement.

Figure 11:
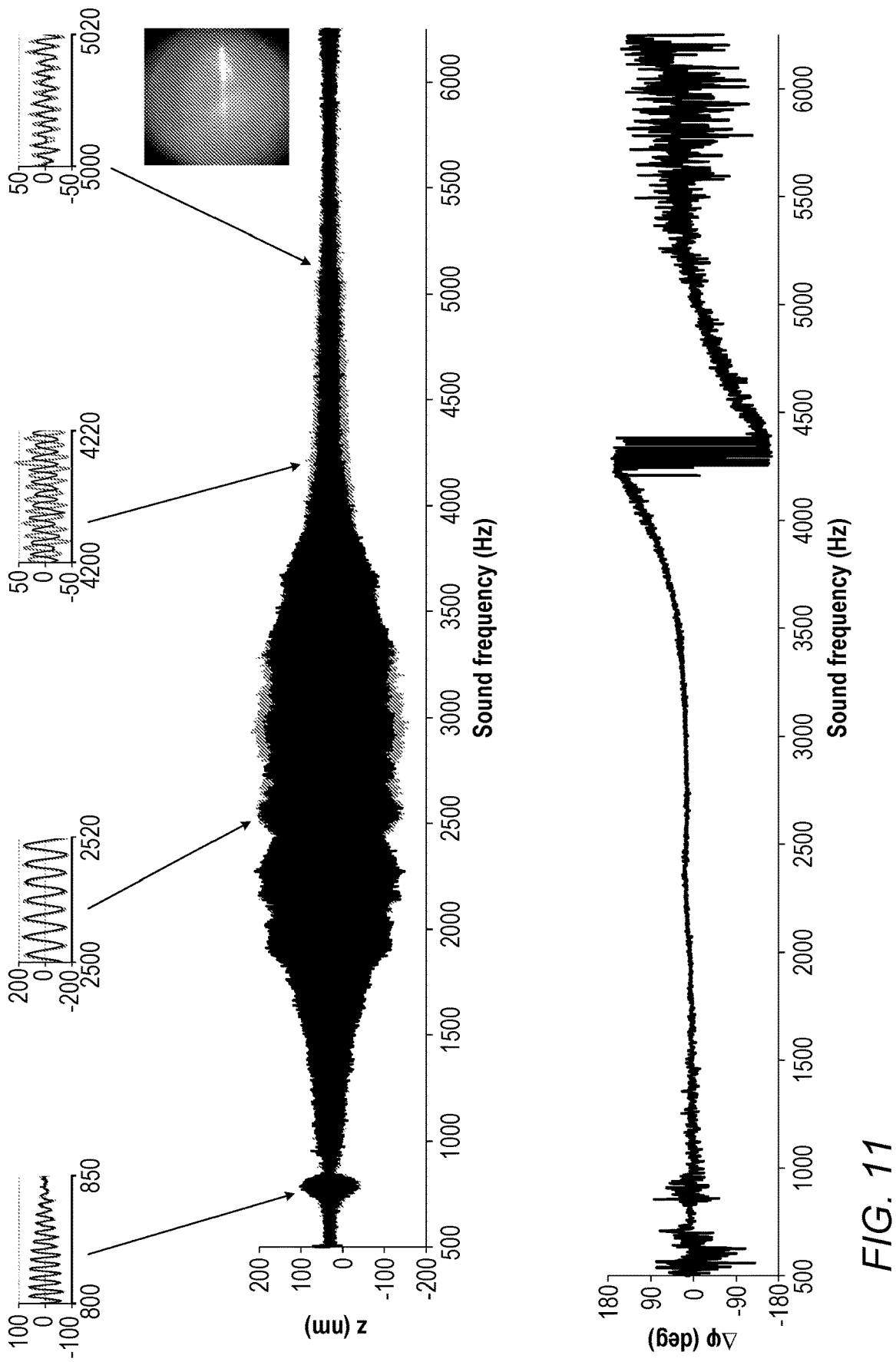
FIG. 11 shows the single-line measurement technique used for measuring the frequency response of different parts of the membrane, including their relative phases.

The single-line measurement technique could also be useful for measuring the frequency response of different parts of the membrane, including their relative phases, as illustrated in FIG. 11. To demonstrate this capability, the imaging line was kept at its position between the umbo and the cone of light, as shown in the top-right inset of FIG. 11, the line camera was set to a constant 50 kHz line rate, and a linear excitation frequency chirp was applied between 500 Hz and 6,250 Hz. The periodic displacements of both umbo and cone-of-light followed the general frequency response of the sound system, which was not calibrated for this measurement. However, the phase difference between the two points, as shown in the bottom plot, showed constant drift during the sweep: below 2 kHz the two points oscillated with similar phases, with only minor differences (smaller than 15°) up to 3.5 kHz, as apparent from the essentially congruent plots of the umbo and cone-of-light phase shifts shown in the two leftmost plots in the top row of FIG. 11. Between 3.5 kHz and 5 kHz the phase difference increased gradually, with the cone of light lagging behind the umbo point below 4,250 Hz, reaching a complete out-of-phase 180° oscillation at 4,300 Hz (the strong ±π jumps is an artifact caused by noise on the wrapped phase), and oscillating ahead of the umbo up to 5,000 Hz, where the two points returned to in-phase oscillation. These phase shifts are clearly shown in the top row of plots, taken over small frequency ranges of the total range.

Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. Furthermore, it is appreciated by persons skilled in the art that the present invention is not limited by what has been particularly shown and described hereinabove. Rather the scope of the present invention includes both combinations and subcombinations of various features described hereinabove as well as variations and modifications thereto which would occur to a person of skill in the art upon reading the above description and which are not in the prior art.

We claim:

1. A system for determining the vibrational characteristics of a single line across a tympanic membrane of a subject, the system comprising:
   a light source adapted to input into the system, a beam of the light having a range of wavelengths;
   a diffracting element configured to spectrally disperse the beam of light along the single line;
   a lens system configured to focus the single line of spectrally dispersed light through the auditory canal of a subject, such that it impinges on the tympanic membrane of the subject;
   a control system adapted to determine from a spectrometric analysis of light resulting from the interference of the spectrally dispersed light reflected from the tympanic membrane with a reference beam, the vibrational amplitude of motion of the tympanic membrane as a function of position along the single line,
   wherein the spectral dispersion of the beam of light along the single line enables the system to provide the vibrational characteristics of the single line across the tympanic membrane over a range of acoustic excitation frequencies, in a time sufficiently short that the accuracy of the measurement of the tympanic membrane vibrational motion is unaffected by in vivo environmental motions.

2. The system according to claim 1 wherein the lens system is further configured to provide wide field imaging of the illuminated single line on the tympanic membrane.

3. The system according to claim 2 further comprising a widefield camera adapted to enable operator guidance of the position of the single line of the beam of light across the tympanic membrane.

4. The system according to claim 1, further comprising a sound source positioned to apply an acoustic signal having the range of excitation frequencies to the tympanic membrane.

5. The system according to claim 4 wherein the sound source is configured to output the acoustic signal amplitude modulated over a range of up to 0 to 90 dB, and where the acoustic frequencies are in a range of up to 0 to 20 KHz.

6. The system according to claim 4 wherein the range of frequencies are obtained either by frequency modulation of the acoustic signal, or by application of a pulse of the acoustic signal, the pulse containing signals over the range of frequencies.

7. The system according to claim 4, wherein a frequency response of separate parts of the tympanic membrane along the single line can be determined.

8. The system according to claim 1, further comprising a mechanical scanning element configured to adjust a position of the single line of light on the membrane.

9. The system according to claim 8, wherein the controller is configured to input the position of the single line on the membrane, and to output a signal to align the scanning element, such that the single line of light maintains its position in spite of mutual motion between the system and the membrane.

10. The system according to claim 9, wherein the position of the line of light on the membrane is determined using image processing of a camera image of the membrane.

11. The system according to claim 1, wherein the diffracting element and lens system are disposed within an otoscope or an endoscope.

12. The system according to claim 1, wherein the light source has a predefined polarization, and paths along which the light passes essentially maintain the polarization of the light passing therethrough.

13. The system according to claim 1, wherein the light source comprises a swept wavelength source, such that the diffracting element temporally disperses a spot of light along the line, the spot having varying wavelength according to time varying wavelengths of the swept source.

14. The system according to claim 8, wherein the mechanical scanning element is controlled to align the single line of light such that it includes at least one of the umbo region and the malleus region.

15. A method of reducing the time required to determine the vibrational characteristics of a single line across a tympanic membrane of a subject, the method comprising:
   applying an acoustic excitation to the ear of the subject from a sound source;
   inputting a beam of the light having a range of wavelengths into the ear of the subject;
   spectrally dispersing the beam of light using a diffracting element, such that it forms the single line across the tympanic membrane;
   focusing the single line of spectrally dispersed light with a lens system through the auditory canal of the subject, such that it impinges on the tympanic membrane of the subject; and
   determining from a spectrometric analysis of light resulting from the interference of the spectrally dispersed light reflected from the tympanic membrane with a reference beam, the vibrational amplitude and relative phase of motion of the tympanic membrane as a function of position along the single line,
   wherein the spectral dispersion of the beam of light along the single line enables a reduction of the time taken for a measurement of vibrational characteristics of any point along the single line on the tympanic membrane over a range of acoustic excitation frequencies, such that the measurement of the tympanic membrane vibrational motion over the range of acoustic excitation frequencies, can be performed within a time such that the measurement is less affected by in vivo motion artifacts.

16. The method according to claim 15, further comprising the steps of using the lens system to provide wide field imaging of the illuminated single line on the tympanic membrane, and of using a wide field camera to enable an operator to guide the position of the single line of the beam of light across the tympanic membrane.

17. The method according to claim 15, wherein the sound source is configured to modulate the acoustic signal amplitude over a range of up to 0 to 90 dB, and to contain frequencies in a range of up to 0 to 20 KHz.

18. The method according to claim 15, wherein the range of acoustic excitation frequencies are obtained either by frequency modulation of the acoustic signal, or by application of a pulse of the acoustic signal, the pulse containing signals over the range of frequencies.

19. The method according to claim 15, further comprising the step of determining the frequency response of separate parts of the tympanic membrane along the single line.

20. The system according to claim 1, where the range of acoustic excitation frequencies is a swept range of frequencies.

21. The method according to claim 15, wherein the range of acoustic excitation frequencies is a swept range of frequencies.

* * * * *